United States Patent [19]

Eller

[11] Patent Number: 5,453,534

[45] Date of Patent: Sep. 26, 1995

[54] PREPARATION OF ALKOXYCARBOXYLIC ACID ESTERS

[75] Inventor: Karsten Eller, Ludwigshafen, Germany

[73] Assignee: BASF Aktiengesellschaft, Ludwigshafen, Germany

[21] Appl. No.: 266,142

[22] Filed: Jun. 27, 1994

[30] Foreign Application Priority Data

Jul. 1, 1993 [DE] Germany .............. 43 21 871.7

[51] Int. Cl.⁶ .................................................. C07C 69/708
[52] U.S. Cl. .............. 560/187; 560/60; 560/61; 560/126; 560/145
[58] Field of Search .............. 560/187, 60, 61, 560/126, 145

[56] References Cited

U.S. PATENT DOCUMENTS

5,037,511  8/1991  Dornhagen et al. .............. 203/37

FOREIGN PATENT DOCUMENTS

| 0031252 | 7/1981 | European Pat. Off. . |
| 0148626 | 7/1985 | European Pat. Off. . |
| 2164636 | 3/1986 | United Kingdom . |
| 2179563 | 3/1987 | United Kingdom . |

OTHER PUBLICATIONS

J. March, Advanced Organic Chemistry, 3rd Ed. (1985) pp. 342–343.
Kirk–Othmer, Encyclopedia of Chemical Technology, 3rd Ed., (1980) vol. 9, pp. 384–385.
Wade et al, J. Colloid Interface Sci. 21 (1966) pp. 349–357.

Primary Examiner—José G. Dees
Assistant Examiner—Barbara S. Frazier
Attorney, Agent, or Firm—John H. Shurtleff

[57] ABSTRACT

A process for the preparation of alkoxycarboxylic acid esters of the general formula I

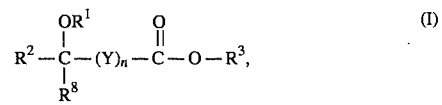

in which Y denotes $CR^4R^5$ or $CR^4R^5$–$CR^6R^7$, $R^1$, $R^2$, $R^3$, $R^4$, $R^5$, $R^6$, $R^7$, $R^8$ denote $C_1$–$C_{20}$alkyl, $C_3$–$C_8$cycloalkyl, aryl, $C_7$–$C_{20}$aralkyl, and $C_7$–$C_{20}$alkylaryl and $R^2$, $R^4$, $R^5$, $R^6$, $R^7$, $R^8$ can additionally denote hydrogen, and n is 0 or 1, by the reaction of hydroxycarboxylic acid esters of the general formula II

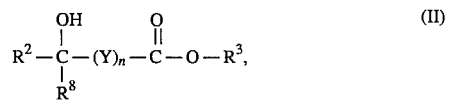

in which $R^2$, $R^3$, $R^8$, Y, and n have the aforementioned meanings, with alcohols of the general formula III $$R_1\text{—OH} \qquad (III),$$

in which $R^1$ has the aforementioned meanings, in the presence of heterogeneous catalysts at temperatures ranging from 100° to 400° C. and pressures ranging from 0.01 to 150 bar, wherein the heterogeneous catalysts used are zeolites and/or hydrothermally prepared phosphates.

11 Claims, No Drawings

PREPARATION OF ALKOXYCARBOXYLIC ACID ESTERS

The present invention relates to a process for the preparation of alkoxycarboxylic acid esters by the reaction of hydroxycarboxylic acid esters with alcohols in the presence of zeolites or hydrothermally prepared phosphates at elevated temperatures.

Unsymmetrical ethers can be prepared by Williamson-Synthesis (cf eg J. March, *Advanced Organic Chemistry*, Wiley, New York, 3rd Ed., 1985, pp. 342–343, or Kirk-Othmer, *Encyclopedia of Chemical Technology*, Wiley, New York, 3rd Ed., 1980, Vol. 9, pp. 384–385. The drawback of this synthesis is the two-stage reaction and the unavoidable formation of salt-like linked products.

It is known that acidic catalysts such as $Al_2O_3$ (Wade et al, *J. Colloid Interface Sci.* 21, 1966, 349–357) can be used for the formation of symmetrical ethers.

Thus, eg, EP 148,626 describes the formation of dimethyl ether from synthesis gas via methanol, formed as intermediate, over aluminosilicates specially pretreated with nitrogen compounds, but the conversions mentioned are low.

E-A 340,324 describes an industrial synthesis of dimethyl ether from methanol over $\gamma$-$Al_2O_3$-catalysts containing small amounts of $SiO_2$ (<1%).

GB-A 2,164,636 and GB-A 2,179,563 describe the use of synthetic beidellitesmectite or of modified montmorillonites for symmetrical etherifications of n-pentanol to form 1,1-dipentyl ether.

EP-A 31,252 discloses the use of bentonites, which yields, in addition to the desired symmetrical ethers, at the same time considerable amounts of alkenes due to dehydration of the alcohols.

It was thus the object of the present invention to overcome the aforementioned drawbacks.

Accordingly, there has been found a new and improved process for the preparation of alkoxycarboxylic acid esters of the general formula I

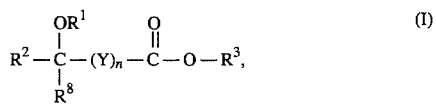

in which

Y denotes $CR^4R^5$ or $CR^4R^5$–$CR^6R^7$, $R^1$, $R^2$, $R^3$, $R^4$, $R^5$, $R^6$, $R^7$, $R^8$ denote $C_1$–$C_{20}$alkyl, $C_3$–$C_8$cycloalkyl, aryl, $C_7$–$C_{20}$aralkyl, and $C_7$–$C_{20}$alkylaryl and $R^2$, $R^4$, $R^5$, $R^6$, $R^7$, $R^8$ can additionally denote hydrogen, and n is 0 or 1, by the reaction of hydroxycarboxylic acid esters of the general formula II

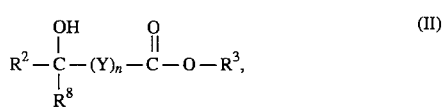

in which $R^2$, $R^3$, $R^8$, Y, and n have the aforementioned meanings, with alcohols of the general formula III

in which $R^1$ has the aforementioned meanings, in the presence of heterogeneous catalysts at temperatures ranging from 100° to 400° C. and pressures ranging from 0.01 to 150 bar, wherein the heterogeneous catalysts used are zeolites and/or hydrothermally prepared phosphates.

The process of the invention can be carried out as follows:

The educts hydroxycarboxylic acid ester II and alcohol III can be passed, either as a mixture or individually, in the liquid or, preferably, gaseous state, to a reactor packed with a heterogeneous catalyst, preferably over fixed-bed catalysts in linear or spiral reactors, for example, by way of a pre-evaporator, and caused to react at temperatures ranging from 100° to 400° C., preferably from 150° to 350° C. and more preferably from 180° to 320° C. and pressures of from 0.01 to 150 bar, preferably from 0.1 to 5 bar more preferably under standard pressure (atmospheric pressure). The temperature of reaction can be preferably such that it is above the evaporation point of the most difficultly volatile component. Temperatures which are too high favor the formation of symmetrical ethers.

Advantageously, the starting point is a pre-made mixture pumped from a storage vessel. The reaction can be carried out in the presence of an inert stream of carrier gas, such as nitrogen, carbon dioxide, or argon.

In a preferred embodiment of the process of the invention the reaction is carried out using 10–75 wt % strength alcoholic solutions of hydroxycarboxylic acid esters II. Suitable alcohols are $C_1$–$C_{20}$alkanols, preferably $C_1$–$C_8$alkanols and more preferably $C_1$–$C_4$alkanols such as methanol, ethanol, n-propanol, isopropanol, n-butanol, isobutanol, sec-butanol, and tert-butanol.

The formation of the hydroxycarboxylic acid esters is preferably made possible in situ by using a mixture of acid and alcohol which is esterified under the reaction conditions in contact with the catalyst. In this embodiment of the invention, it is thus possible to obtain the alkoxycarboxylic acid ester from the hydroxycarboxylic acid in a single step.

The heterogeneous catalysts can either be dried before they are placed in the reactor, or drying can take place in the reactor itself prior to the reaction. Advantageously, this is achieved by using temperatures above the boiling point of water and below the conversion or melting temperature of the molecular sieve crystals, particularly advantageous temperatures being between 300° and 600° C.

Spent heterogeneous catalyst can be regenerated by burning off the deposited coke. This regeneration can take place outside or inside the reactor. Regeneration has a more lasting effect and is more thorough when carried out in the presence of air or oxygen. It has been found to be advantageous to pass air through the reactor at temperatures between 300° and 600° C.

Suitable heterogeneous catalysts are zeolites, preferably zeolites in the mordenite group, zeolites of medium pore size such as those of the pentasil class, ZSM-5, or fine-pored zeolites of the erionite or chabasite class or zeolites of the faujasite class, e.g., X-type, Y-type or L-type zeolites. The last group also includes the so-called "ultrastable" zeolites of the faujasite class, i.e., dealuminated zeolites. Likewise phosphates having a zeolite structure can be used, ie aluminophosphates (AlPO's) such as AlPO-5, AlPO-9, AlPO-11, AlPO-12, AlPO-14, etc., or silicoaluminophosphates (SAPO's) such as SAPO-5, SAPO-11, SAPO-31, and SAPO-34.

Particularly preferred catalysts are X-type zeolites in the alkali or alkaline earth form or hydrothermally prepared phosphates, preferably aluminophosphates (AlPO's) or silicoaluminophosphates (SAPO's).

By 'zeolites' are meant crystalline aluminosilicates having a high-order structure with a three-dimensional network of $SiO_4$ and $AlPO_4$-tetrahedrons interconnected by mutual oxygen atoms. The ratio of the Si and Al atoms to oxygen is 1:2 (cf *Ullmanns Enzyklopädie der technischen Chemie*, Verlag Chemie, Weinheim, 4th Edition, 1983, Vol. 24, p. 575). The electrovalence of the aluminum-containing tetrahedron is balanced by the inclusion of cations in the crystal, eg, alkali ions or hydrogen ions. Cation exchange is possible. The spaces between the tetrahedrons are filled with molecules of water prior to dehydration by drying or calcination.

The zeolites are mostly used in the acid H-form or in the neutral alkali form. Elements other than aluminum, such as B, Ga, Fe, Cr, V, As, Sb, Bi, Be or mixtures thereof can be incorporated in the lattice of the zeolites, or the silicon can be replaced by some other tetravalent element, such as Ge, Ti, Zr, or Hf.

Zeolites are divided into different groups according to their structure. A summary of such structures can be found in the literature (W. M. Meier and D. H. Olson, *Atlas of Zeolite Structure Types*, Butterworths, London, 2nd Ed., 1987).

A diversity of processes for the preparation of zeolites has been described. The aluminophosphates used for the process of the invention are, in particular, aluminophosphates which have been synthesized under hydrothermal conditions. For example AlPO-5 is synthesized by homogeneously mixing orthophosphoric acid and pseudoboehmite (Captal SB®) in water, adding tetrapropylammonium hydroxide to this mixture and then allowing the mixture to react at approximately 150° C. for from 20 to 60 h under autogenous pressure in an autoclave. The AlPO-5 obtained as filtrate is dried at from 100° to 160° C. and calcined at from 450° to 550° C. SAPO-5 is, for example, obtained by mixing $SiO_2$, suspended in an aqueous tetrapropylammonium hydroxide solution, with an aqueous suspension of pseudoboehmite and orthophosphoric acid and causing subsequent reaction of the mixture at from 150° to 200° C. over a period of from 20 to 200 h under autogenous pressure in a stirred autoclave. Drying of the powder obtained as filtrate takes place at from 110° to 160° C. and calcination at from 450° to 550° C.

The substituents Y, $R^1$, $R^2$, $R^3$, $R^4$, $R^5$, $R^6$, $R^7$, $R^8$ and the index n have the following meanings, Y
  $CR^4R^5$ or $CR^4R^5$–$CR^6R^7$,
$R^1$, $R^2$, $R^3$, $R^4$, $R^5$, $R^6$, $R^7$, $R^8$
  $C_1$–$C_{20}$alkyl, preferably $C_1$–$C_8$alkyl more preferably $C_1$–$C_4$alkyl such as methyl, ethyl, n-propyl, isopropyl, n-butyl, isobutyl, sec-butyl, and tert-butyl,
  $C_3$–$C_8$cycloalkyl, preferably cyclopentyl, cyclohexyl, and cyclooctyl,
  aryl such as phenyl, 1-naphthyl, 2-naphthyl, 1-anthryl, 2-anthryl, and 9-anthryl, preferably phenyl, 1-naphthyl, and 2-naphthyl more preferably phenyl and
  $C_7$–$C_{20}$aralkyl, preferably $C_7$–$C_{12}$phenylalkyl such as benzyl, 1-phenethyl, 2-phenethyl, 1-phenylpropyl, 2-phenylpropyl, 3-phenyl-propyl, 1-phenylbutyl, 2-phenylbutyl, 3-phenylbutyl, and 4-phenylbutyl more preferably benzyl, 1-phenethyl, and 2-phenethyl.
  $C_7$–$C_{20}$alkylaryl, preferably $C_7$–$C_{12}$alkylphenyl such as 2-methylphenyl, 3-methylphenyl, 4-methylphenyl, 2,4-dimethyl-phenyl, 2,5-dimethylphenyl, 2,6-dimethylphenyl, 3,4-dimethyl-phenyl, 3,5-dimethylphenyl, 2,3,4-trimethylphenyl, 2,3,5-trimethylphenyl, 2,3,6-trimethylphenyl, 2,4,6-trimethylphenyl, 2-ethylphenyl, 3-ethylphenyl, 4-ethylphenyl, 2-n-propylphenyl, 3-n-propylphenyl and 4-n-propylphenyl, $R^2$, $R^4$, $R^5$, $R^6$, $R^7$, $R^8$
  can additionally denote hydrogen, and
n is 0 or 1, preferably 0.

EXAMPLES

The analysis of the products formed was carried out using gas-chromatographical methods, and the products were identified by comparison thereof with authentic material or by means of gas chromatography with mass-spectrometric linkage (GC-MS).

Example 1

Into a spiral reactor of 0.9 cm in diameter and 100 cm in length there are placed 10 g of X-type zeolite (Wako, 1/8" or 1/16" extrudates ground to grit particles), which has been pretreated overnight at 150° C. in a dessicator cabinet. The reactor is heated to 240° C. and a mixture of 25 parts by weight of methyl lactate and 75 parts by weight of methanol is added at a rate of 10 g/h. The mixture of products is collected in a downstream condenser eqipped with a receiver and samples are taken at regular intervals for analysis. After a reaction period of 4 h the conversion of methyl lactate is 94% and the yield of methyl 2-methoxypropionate is 77.6%, and after 8 h these values are 92.4% and 77.2% respectively.

Example 2

In a repetition of Example 1 but using 10 g of zeolite-like alumophosphate AlPO-5 at a reaction temperature of 300° C. there are obtained, after a period of 4 h, a conversion of 72% and a yield of methyl 2-methoxypropionate of 46.9%.

Example 3

In a repetition of Example 1 but using 10 g of silicoalumophosphate SAPO-5 at a reaction temperature of 300° C. there are obtained, after a period of 6 h, a conversion of 91.2% and a yield of methyl 2-methoxypropionate of 27.5%.

Example 4

In a repetition of Example 1 but using 10 g of CaX (molecular sieve 10 Å) at a reaction temperature of 300° C. there are obtained, after a period of 4 h, a conversion of 82% and a yield of methyl 2-methoxypropionate of 45.8%.

Example 5

Into a spiral reactor of 0.9 cm in diameter and 100 cm in length there are placed 10 g of X-type zeolite (Wako, 1/8" or 1/16" extrudates ground to grit particles), which has been pretreated overnight at 150° C. in a dessicator cabinet. The reactor is heated to 260° C. and a mixture of 25 parts by weight of methyl hydroxyacetate and 75 parts by weight of methanol is added at a rate of 10 g/h. The mixture of products is collected in a downstream condenser equipped with a receiver and samples are taken at regular intervals for analysis. After a reaction time of 4 h the conversion of methyl hydroxyacetate is 91.6% and the yield of methyl methoxyacetate is 90.7%.

Example 6

Into a spiral reactor of 0.9 cm in diameter and 100 cm in length there are placed 10 g of X-type zeolite (Wako, ⅛" or ¹⁄₁₆" extrudates ground to grit particles), which has been pretreated overnight at 150° C. in a dessicator cabinet. The reactor is heated to 240° C. and a mixture of 25 parts by weight of ethyl 2-hydroxyhexanoate and 75 parts by weight of methanol is added at a rate of 10 g/h. The mixture of products is collected in a downstream condenser eqipped with a receiver and samples are taken at regular intervals for analysis. After a reaction time of 5 h the conversion of ethyl 2-hydroxyhexanoate is 73.2% and the yield of methyl 2-methoxyhexanoate is 41.2%.

Example 7

Into a linear reactor having a diameter of 0.9 cm and a length of 22.5 cm there are placed 10 g of X-type zeolite (Wako, ⅛" or ¹⁄₁₆" extrudates ground to grit particles) and the batch is dried overnight in the reactor at 260° C. A mixture of 25 parts by weight of methyl lactate and 75 parts by weight of methanol at the same temperature is pumped in at a rate of 8 g/h. The mixture of products is collected in a downstream condenser eqipped with a receiver and samples are taken at regular intervals for analysis. Following a reaction time of 24 h the conversion is 90.8% and the yield of methyl 2-methoxypropionate is 80.7%.

Example 8

Into a linear reactor having a diameter of 0.9 cm and a length of 22.5 cm there are placed 10 g of X-type zeolite (Wako, ⅛" or ¹⁄₁₆" extrudates ground to grit particles) which has been pretreated in a dessicator cabinet overnight at 150° C. A mixture of 25 parts by weight of methyl lactate and 75 parts by weight of methanol is pumped in at a rate of 10 g/h. The outlet of the reactor is controlled by a regulating valve such that it opens only when an internal pressure of 80 bar is reached. Following a period of 7 h the conversion is 86.8% and the yield of methyl 2-methoxypropionate is 65.6%.

Example 9

Into a spiral reactor of 0.9 cm in diameter and 100 cm in length there are placed 10 g of X-type zeolite (Wako, ⅛" or ¹⁄₁₆" extrudates ground to grit particles), which has been pretreated overnight at 150° C. in a dessicator cabinet. The reactor is heated to 240° C. and a mixture of 25 parts by weight of methyl lactate and 75 parts by weight of ethanol is added at a rate of 10 g/h. The mixture of products is collected in a downstream condenser eqipped with a receiver and samples are taken at regular intervals for analysis. After a reaction time of 1 h the conversion of methyl lactate is 100%, the yield of methyl 2-methoxypropionate is 1.4%, the yield of ethyl 2-methoxypropionate is 2.2%, the yield of methyl 2-ethoxypropionate is 6.0%, and the yield of ethyl 2-ethoxypropionate is 13.6%. The yield of the transesterification product ethyl lactate is 2.1%.

We claim:

1. A process for the preparation of an alkoxycarboxylic acid ester of the formula

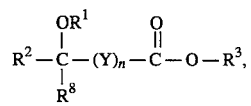

in which Y is $CR^4R^5$ or $CR^4R^5-CR^6R^7$ while n is 0 or 1, each of the substituents $R^1$, $R^2$, $R^3$, $R^4$, $R^5$, $R^6$, $R^7$ and $R^8$ is selected from the group consisting of $C_1$–$C_{20}$-alkyl, $C_3$–$C_8$-cycloalkyl, aryl, $C_7$–$C_{20}$-aralkyl, and $C_7$–$C_{20}$-alkylaryl with the proviso that each of $R^2$, $R^4$, $R^5$, $R^6$, $R^7$ and $R^8$ can additionally denote hydrogen, which process comprises:

reacting a hydroxycarboxylic acid ester of the formula

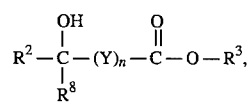

in which $R^2$, $R^3$, $R^8$, Y and n have the aforementioned meanings, with an alcohol of the formula $$R^1\text{—OH} \qquad \qquad \text{III,}$$

in which $R^1$ has the aforementioned meanings, in the presence of a heterogeneous catalyst selected from the group consisting of zeolites and hydrothermally prepared aluminophosphates or silicoaluminophosphates at temperatures ranging from 100° to 400° C. and pressures ranging from 0.01 to 150 bar.

2. A process for the preparation of an alkoxycarboxylic acid ester I as defined in claim 1, wherein n is equal to 0.

3. A process for the preparation of an alkoxycarboxylic acid ester I as defined in claim 1, wherein $R^2$ denotes hydrogen or methyl, $R^8$ denotes hydrogen and n is equal to 0.

4. A process for the preparation of an alkoxycarboxylic acid ester I as defined in claim 1, wherein $R^1$ stands for methyl.

5. A process as claimed in claim 1, wherein the zeolite used is an X-type or Y-type zeolite in the alkali or alkaline earth form.

6. A process as claimed in claim 1, wherein the hydrothermally prepared phosphate used is an aluminophosphate or silicoaluminophosphate.

7. A process as claimed in claim 1, wherein the reaction is carried out using a 10–75 wt % strength alcoholic solution of hydroxycarboxylic acid ester.

8. A process as claimed in claim 1, wherein the hydroxycarboxylic acid ester reactant II is prepared in situ by using a mixture of an acid alcohol which is esterified under the reaction conditions in the presence of said catalyst.

9. A process as claimed in claim 1, wherein the reaction is carried out at a temperature of from 150° to 350° C. and at a pressure of from 0.1 to 5 bar.

10. A process as claimed in claim 1, wherein the reaction is carried out at a temperature of from 180° to 320° C.

11. A process as claimed in claim 1, wherein the reaction is carried out under atmospheric pressure.

* * * * *